(12) United States Patent
Ray et al.

(10) Patent No.: US 9,096,323 B1
(45) Date of Patent: Aug. 4, 2015

(54) WINDOW CONTAMINATION SENSOR FOR OPTICAL DETECTION SYSTEMS

(71) Applicant: Rosemount Aerospace Inc., Burnsville, MN (US)

(72) Inventors: Mark Ray, Burnsville, MN (US); Kaare Josef Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 0 days.

(21) Appl. No.: 14/250,206

(22) Filed: Apr. 10, 2014

(51) Int. Cl.
*G01J 4/00* (2006.01)
*B64D 15/20* (2006.01)
*G01N 21/958* (2006.01)

(52) U.S. Cl.
CPC .............. *B64D 15/20* (2013.01); *G01N 21/958* (2013.01); *G01J 4/00* (2013.01); *G01N 2201/06113* (2013.01)

(58) Field of Classification Search
CPC .................. G01N 21/958; G01N 2201/06113; B64D 15/20; G01J 4/00
USPC ....................................................... 356/369
See application file for complete search history.

(56) References Cited

U.S. PATENT DOCUMENTS

| | | | |
|---|---|---|---|
| 4,435,093 A | 3/1984 | Krause et al. | |
| 4,529,881 A | 7/1985 | Cuervels et al. | |
| 5,838,239 A * | 11/1998 | Stern et al. | 340/583 |
| 6,069,565 A * | 5/2000 | Stern et al. | 340/583 |
| 7,876,450 B2 * | 1/2011 | Novotny et al. | 356/491 |
| 7,986,408 B2 | 7/2011 | Ray et al. | |
| 8,144,325 B2 | 3/2012 | Ray et al. | |
| 8,320,424 B2 | 11/2012 | Bolt et al. | |
| 8,338,785 B2 | 12/2012 | Ray | |
| 2013/0103316 A1 | 4/2013 | Ray et al. | |
| 2013/0103317 A1 | 4/2013 | Ray et al. | |

* cited by examiner

*Primary Examiner* — Roy M Punnoose
(74) *Attorney, Agent, or Firm* — Kinney & Lange, P.C.

(57) ABSTRACT

A system for detecting contamination of a window of an optical system includes a polarizing beamsplitter, a quarter waveplate, a photodetector, and a processor. The polarizing beamsplitter is configured to receive a laser beam having a first polarization and reflect the laser beam having the first polarization to the window. The photodetector is configured to sense a magnitude of reflections of the laser beam from the window having a second polarization, wherein the polarizing beamsplitter passes the reflections of the laser beam from the window having the second polarization to the photodetector. The processor is configured to determine a contamination level of the window based upon the magnitude of the reflections of the laser beam from the window.

14 Claims, 3 Drawing Sheets

WINDOW CONTAMINATION SENSOR FOR OPTICAL DETECTION SYSTEMS

BACKGROUND

The present invention relates generally to optical detection systems, and in particular to a system and method for detecting contamination of a window of an optical detection system.

Aircraft systems often include, for example, icing detection systems such as those described in U.S. Pat. No. 7,986,408. These systems may send out, for example, a pulsed laser beam with a selected polarization. The beam is projected out of the aircraft and into, for example, a cloud. A receiver lens receives backscatter of the beam from the cloud and utilizes a plurality of high sensitivity photodetectors to sense the backscatter of the beam. The sensed backscatter may be interpreted to determine, for example, an icing condition.

The pulsed laser beam of these systems may be provided to the cloud through, for example, a window. These windows are subject to the accumulation of contaminants which can degrade optical transmission and compromise the quality of the measurements. It is desirable to provide continuous and autonomous detection of window contamination in order to alert aircraft personnel of the loss of data integrity and the need for manual cleaning of the window.

In aircraft icing conditions detection systems, it is aerodynamically desirable for the entire system to be flush-mounted with the skin of the aircraft. Prior art systems, such as those described in U.S. Pat. Nos. 7,948,628 and 8,320,424, implement window cleanliness detectors. These systems, however, include components located on an external side of the window. For example, an external mirror may be mounted outside the window to reflect the beam back through the window into a cleanliness detector. Components external to the window eliminate the aerodynamic advantages of a flush-mounted optical detection system.

SUMMARY

A system for detecting contamination of a window of an optical system includes a polarizing beamsplitter, a photodetector, and a processor. The polarizing beamsplitter is configured to receive a laser beam having a first polarization and reflect the laser beam having the first polarization to the window. The photodetector is configured to sense a magnitude of reflections of the laser beam from the window having a second polarization orthogonal to the first polarization, wherein the polarizing beamsplitter passes the reflections of the laser beam from the window having the second polarization to the photodetector. The processor is configured to determine a contamination level of the window based upon the magnitude of the reflections of the laser beam from the window.

DETAILED DESCRIPTION

Window contamination detection for an optical system is disclosed herein that includes a photodetector configured to sense reflections of a laser beam to detect a contamination level of a window. The system includes a photodetector and a polarizing beamsplitter. A pulsed laser is provided to the polarizing beamsplitter. The polarizing beamsplitter directs the laser through a window based upon the linear polarization state of the beam. A reflection of the beam off the window, after traversing a quarter waveplate twice, has an orthogonal polarization state to that of the laser beam and thus, the reflection passes through the polarizing beamsplitter to the photodetector. The photodetector senses the reflection and provides an output indicative of a magnitude of the reflected light. The greater the contamination of the window, the greater the reflection of the beam from the window. Therefore, the output of the photodetector may be interpreted by a signal processor to determine a level of contamination of the window.

Figure 1:
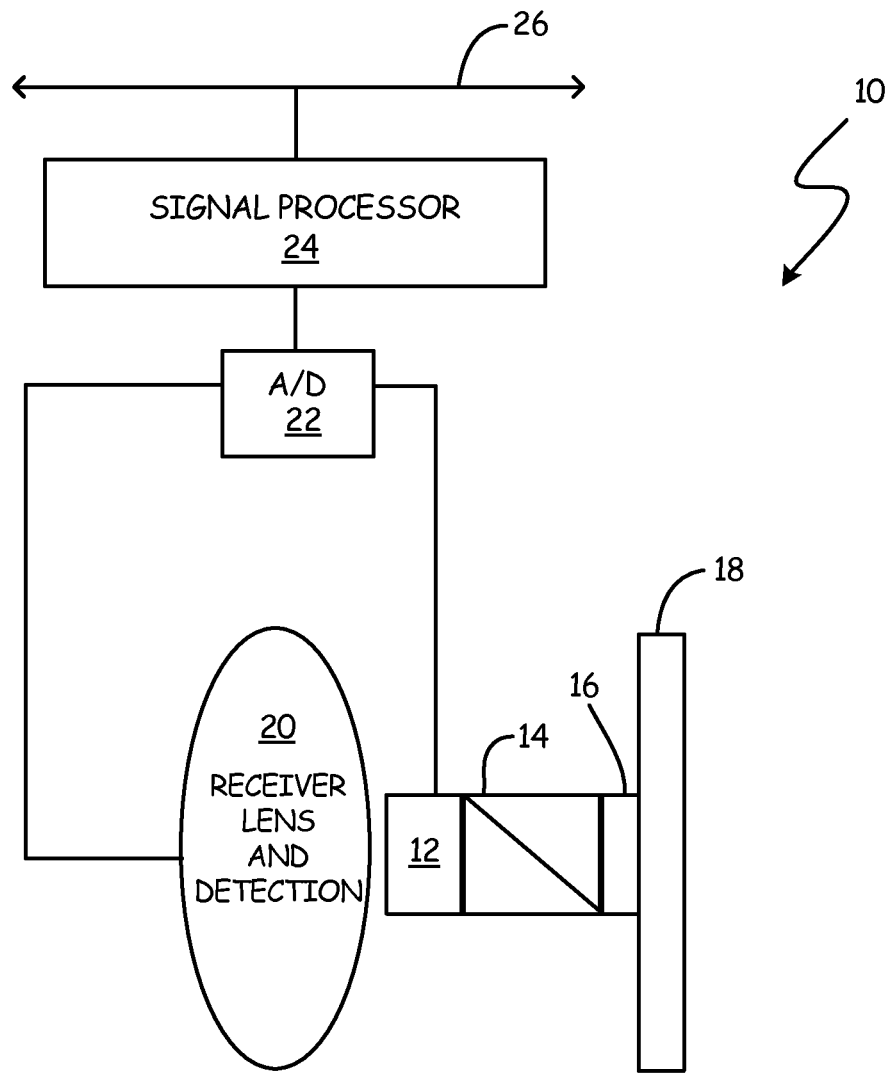
FIG. 1 is a diagram that illustrates a system for detecting window contamination within an aircraft optical detection system.

FIG. 1 is a diagram that illustrates system 10 for detecting window contamination within an aircraft optical system. System 10 includes photodetector 12, polarizing beamsplitter 14, quarter waveplate 16, window 18, receiver lens and detection elements 20, analog-to-digital converter 22, signal processor 24, and communications bus 26. System 10 is, for example, part of an aircraft lidar icing detection system. Window 18 may be, for example, two inches in diameter and flush-mounted with a skin of the aircraft, which may lead to the accumulation of contaminants.

Figure 2:
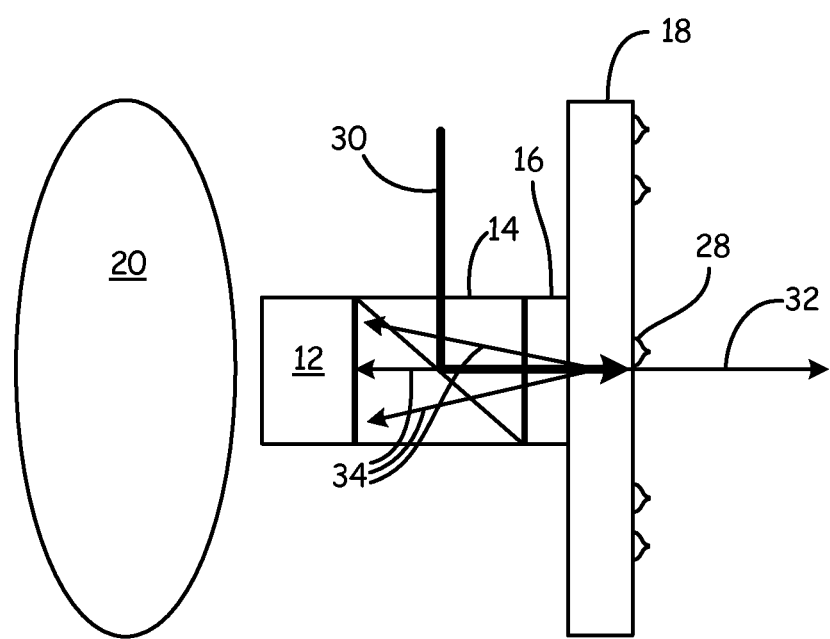
FIG. 2 is a diagram that illustrates reflections of a beam of an optical detection system caused by contaminants on a window.

With continued reference to FIG. 1, FIG. 2 is a diagram illustrating system 10 with contaminants 28 accumulated on window 18. Beam 30 is provided to polarizing beamsplitter 14 from, for example, any optical laser or other light source. Beam 30 is, for example, linearly polarized. Polarizing beamsplitter 14 may be, for example, a polarizing beamsplitter configured to direct beam 30 to window 18 based upon the polarization of beam 30. The beam passes through quarter waveplate 16 to window 18. Quarter waveplate 16 circularly polarizes the beam. The circularly polarized beam 30 is provided through window 18 to, for example, a cloud.

During normal operation of the optical detection system, beam 30 may be pulsed at a rate of, for example, tens of kilohertz. Backscatter from the cloud through window 18 is received by the receiver lens and detection elements 20. Receiver lens and detection elements 20 may include, for example, a plurality of high sensitivity photodetectors to sense the backscatter from the cloud through the receiver lens. Contaminants 28 may occlude both beam 30 from passing through window 18 and the backscatter from passing back through window 18, and thus affect detection of the condition for which the optical detection system is designed. Therefore, it is desirable to detect contamination of window 18.

When beam 30 strikes window 18, reflections 34 of beam 30 are reflected back toward polarizing beamsplitter 14. Reflections 34 may be caused both by window 18 as well as contaminants 28. Due to the change in propagation direction, reflections 34 may be orthogonal to the polarization of beam 30. Quarter waveplate 16 and polarizing beamsplitter 14 act as an optical isolator for reflections 34 of orthogonal polarization to beam 30. Reflections 34 of orthogonal polarization to beam 30 therefore pass through polarizing beamsplitter 14 toward receiver lens and detection elements 20. In past systems, a light baffle may have been implemented to prevent reflections 34 that pass through polarizing beamsplitter 14 from saturating the highly sensitive photodetectors of receiver lens and detection elements 20.

In replacement of the prior art light baffles, photodetector 12 is implemented to receive reflections 34 and provide an indication of the magnitude of reflections 34 to analog-to-digital converter 22. Analog-to-digital converter 22 converts the signal from photodetector 12 into a digital signal for processor 24. Photodetector 12 may be, for example, any device capable of sensing reflections 34 and may be implemented, for example, as an optical band-pass filter tuned to the wavelength of beam 30. Photodetector 12 may have a low enough sensitivity to prevent saturation by reflections 34 while still providing accurate measurements for contaminant detection. In this way, photodetector 12 may be utilized to both prevent saturation of the high sensitivity photodetectors of receiver lens and detection elements 20 and to sense a magnitude of reflections 34 to detect contamination of window 18.

Contaminants 28 in the path of beam 30 may create a detriment to the function of the optical detection system. If, for example, contaminants 28 form a small, opaque splotch on window 18, it will not greatly affect the function of the optical detection system if the splotch is located on a portion of window 18 that receives the backscattered light because the backscattered light is spread to large area of window 18. However, if the splotch is directly on a portion of window 18 through which beam 30 travels, the function of the optical detection system may be greatly diminished as a result of the splotch nearly extinguishing beam 30, causing a loss of nearly all sensitivity of the optical detection system. By measuring reflections 34 of beam 30, system 10 is capable of detecting both this condition as well as the common condition of uniform contamination of window 18 caused by dust, grease, hydraulic fluids, or other contaminants.

Figure 3A:
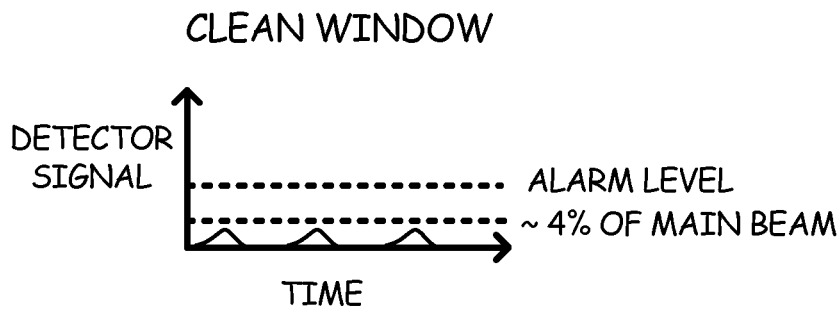
FIGS. 3A-3C are waveforms illustrating sensed signals for varying levels of window contamination for an optical detection system.
Figure 3B:
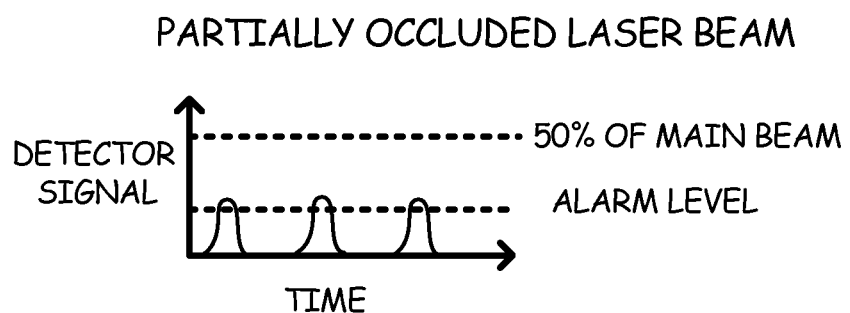
Figure 3C:
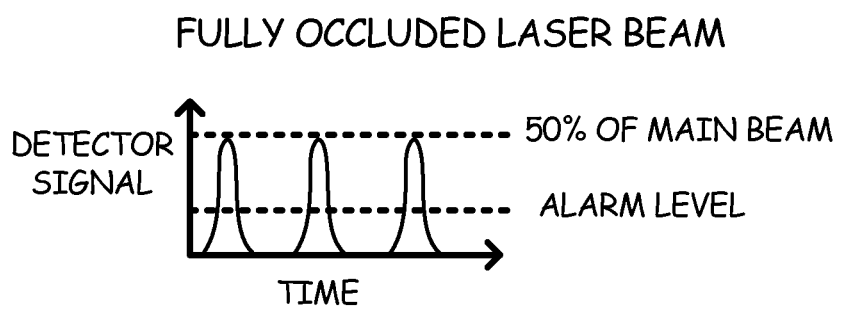

With continued reference to FIGS. 1 and 2, FIGS. 3A-3C are waveforms illustrating outputs of photodetector 12 for varying levels of contamination of window 18. FIG. 3A is a waveform that illustrates a condition in which, for example, window 18 has no contamination. FIG. 3B is a waveform that illustrates a condition in which, for example, window 18 is contaminated above a threshold level. FIG. 3C is a waveform that illustrates a condition in which, for example, window 18 is fully contaminated.

In conditions for which window 18 contains no contaminants 28, there may be a minimal amount of reflection 34 such as, for example, four percent of beam 30. Window 18 may, for example, have an anti-reflection coating. Typical anti-reflection coatings limit reflections 34 to 0.5-2.0% of beam 30 at each surface. As illustrated in FIG. 3A, photodetector 12 senses the limited reflections 34 when window 18 contains no contaminants. Because of this, a threshold level may be selected that is greater than the minimal reflection value in order to avoid false detection of contaminants.

Contaminants 28 may increase the magnitude of reflections 34. It is possible that contaminants 28 may absorb, rather than reflect, beam 30, however, beam 30 may have a wavelength that lies outside the absorption range of common contaminants such as dust, oil, and hydraulic fluid. This wavelength may be, for example, approximately nine hundred and five nanometers. Most contaminants 28 may also depolarize beam 30 causing reflections 34 to be depolarized. In the case of depolarization, half of reflections 34 will be directed by polarizing beamsplitter 14 to retrace the path of beam 30, while the other half will pass through polarizing beamsplitter 14 to photodetector 12. Therefore, as illustrated in FIG. 3C, full contamination of window 18 and depolarization of beam 30 may be indicated by a magnitude of reflections 34 of fifty percent of beam 30.

A threshold level may be selected for any magnitude between the minimum reflection magnitude and the maximum reflection magnitude. The threshold level is any level for which it is desirable to clean window 18. Processor 24 receives the magnitude of reflections 34 from photodetector 12 through analog-to-digital converter 22. Processor 24 compares the magnitude of reflections 34 with, for example, the threshold level. In response to the magnitude of reflections 34 being greater than the threshold value, as illustrated in FIGS. 3B and 3C, processor 24 may provide an indication on bus 26 of contamination of window 18. This indication may be provided to, for example, a pilot of the aircraft, or any other person or system that may take action in response to contamination of window 18. Processor 24 may be any electronic circuit capable of comparing the output of photodetector 12 with a threshold value such as, for example, a digital signal processor, a field programmable gate-array (FPGA) or any other digital circuit. Bus 26 is any communication bus such as, for example, a communication bus onboard an aircraft.

In this way, system 10 provides detection of contaminants 28 which can degrade the optical transmission and compromise the quality of measurements of an optical detection system. Photodetector 12 acts as both a baffle to prevent reflections 34 from saturating the high sensitivity devices of receiver lens and detection elements 20 as well as a contamination sensor. All components of system 10 may be located within, for example, the aircraft of the optical detections system. Because of this, window 18 remains flush-mounted with the skin of the aircraft with no additional aerodynamic drag.

Discussion of Possible Embodiments

The following are non-exclusive descriptions of possible embodiments of the present invention.

A system for detecting contamination of a window of an optical system includes a polarizing beamsplitter, a photodetector, and a processor. The polarizing beamsplitter is configured to receive a laser beam having a first polarization and reflect the laser beam having the first polarization to the window. The photodetector is configured to sense a magnitude of reflections of the laser beam from the window having a second polarization orthogonal to the first polarization, wherein the polarizing beamsplitter passes the reflections of the laser beam from the window having the second polarization to the photodetector. The processor is configured to determine a contamination level of the window based upon the magnitude of the reflections of the laser beam from the window.

The system of the preceding paragraph can optionally include, additionally and/or alternatively, any one or more of the following features, configurations and/or additional components:

A further embodiment of the foregoing system, further comprising a quarter waveplate located between the window and the polarizing beamsplitter, wherein the quarter waveplate is configured to convert the first polarization from a linear polarization state into a circular polarization state.

A further embodiment of any of the foregoing systems, wherein the optical system is an aircraft icing detection system.

A further embodiment of any of the foregoing systems, wherein the photodetector comprises a band-pass filter tuned to the wavelength of the laser beam.

A further embodiment of any of the foregoing systems, further comprising a receiver lens, and detection elements configured to sense a backscatter of the laser beam, wherein the photodetector is positioned to prevent saturation of the detection elements by the reflections of the laser beam from the window.

A further embodiment of any of the foregoing systems, further comprising an analog-to-digital converter configured to convert the magnitude of the reflections from the photodetector into a digital signal for the processor, and a communication bus, wherein the processor provides an indication of contamination on the communication bus in response to the magnitude of the reflections being greater than a threshold value.

A method of detecting contamination of a window of an optical system includes, among other things, reflecting, using a polarizing beamsplitter, a laser beam having a first polarization transmitted to the window; receiving, by the polarizing beamsplitter, reflections of the laser beam from the window having a second polarization; passing, using the polarizing beamsplitter, the reflections of the laser beam from the window having the second polarization to a photodetector; sensing, using the photodetector, a magnitude of the reflections of the laser beam; and determining a contamination level of the window based upon the magnitude of the reflections of the laser beam.

The method of the preceding paragraph can optionally include, additionally and/or alternatively, any one or more of the following features, configurations and/or additional components:

A further embodiment of the foregoing method, wherein reflecting, using the polarizing beamsplitter, the laser beam having the first polarization to the window comprises reflecting the laser beam from the polarizing beamsplitter to the window through a quarter waveplate; and converting the first polarization of the laser beam from a linear polarization to circular polarization.

A further embodiment of any of the foregoing methods, wherein reflecting, using the polarizing beamsplitter, the laser beam having the first polarization to the window comprises reflecting the laser beam from the polarizing beamsplitter to the window through a quarter waveplate; and converting the first polarization of the laser beam from a linear polarization to circular polarization.

A further embodiment of any of the foregoing methods, wherein passing, using the polarizing beamsplitter, the reflections of the laser beam to the photodetector comprises optically isolating the reflections of the laser beam using the quarter waveplate and the polarizing beamsplitter.

A further embodiment of any of the foregoing methods, wherein determining a contamination level comprises receiving, by a processor, the magnitude of the reflections of the laser beam; providing, by the processor, an indication of contamination of the window if the magnitude of the reflections of the laser beam are greater than a threshold value.

A further embodiment of any of the foregoing methods, wherein receiving, by the processor, the magnitude of the reflections comprises converting, using an analog-to-digital converter, the magnitude of the reflections into a digital signal.

A further embodiment of any of the foregoing methods, wherein providing, by the processor, the indication of contamination comprises providing the indication on a communications bus.

A further embodiment of any of the foregoing methods, wherein the optical system is an aircraft icing detection system.

A further embodiment of any of the foregoing methods, further comprising blocking, using the photodetector, the reflections of the laser beam from reaching a receiver lens.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for detecting contamination of a window of an optical system, the system comprising:
  a polarizing beamsplitter configured to receive a laser beam having a first polarization and reflect the laser beam having the first polarization to the window;
  a photodetector configured to sense a magnitude of reflections of the laser beam from the window having a second polarization orthogonal to the first polarization, wherein the polarizing beamsplitter passes the reflections of the laser beam from the window having the second polarization to the photodetector; and
  a processor configured to determine a contamination level of the window based upon the magnitude of the reflections of the laser beam from the window.

2. The system of claim 1, further comprising a quarter waveplate located between the window and the polarizing beamsplitter, wherein the quarter waveplate is configured to convert the first polarization from a linear polarization into a circular polarization.

3. The system of claim 1, wherein the optical system is an aircraft icing detection system.

4. The system of claim 1, wherein the photodetector comprises a band-pass filter tuned to the wavelength of the laser beam.

5. The system of claim 1, further comprising:
  a receiver lens; and
  detection elements configured to sense a backscatter of the laser beam, wherein the photodetector is positioned to prevent saturation of the detection elements by the reflections of the laser beam from the window.

6. The system of claim 1, further comprising:
  an analog-to-digital converter configured to convert the magnitude of the reflections from the photodetector into a digital signal for the processor; and
  a communication bus, wherein the processor provides an indication of contamination on the communication bus in response to the magnitude of the reflections being greater than a threshold value.

7. A method of detecting contamination of a window of an optical system, the method comprising:
  reflecting, using a polarizing beamsplitter, a laser beam having a first polarization to the window;
  receiving, by the polarizing beamsplitter, reflections of the laser beam from the window having a second polarization;
  passing, using the polarizing beamsplitter, the reflections of the laser beam from the window having the second polarization to a photodetector;
  sensing, using the photodetector, a magnitude of the reflections of the laser beam; and
  determining a contamination level of the window based upon the magnitude of the reflections of the laser beam.

8. The method of claim 7, wherein reflecting, using the polarizing beamsplitter, the laser beam having the first polarization to the window comprises:

reflecting the laser beam from the polarizing beamsplitter to the window through a quarter waveplate; and converting the first polarization of the laser beam from a linear polarization to circular polarization.

9. The method of claim 8, wherein passing, using the polarizing beamsplitter, the reflections of the laser beam to the photodetector comprises optically isolating the reflections of the laser beam using the quarter waveplate and the polarizing beamsplitter.

10. The method of claim 7, wherein determining a contamination level comprises:

receiving, by a processor, the magnitude of the reflections of the laser beam;

providing, by the processor, an indication of contamination of the window if the magnitude of the reflections of the laser beam are greater than a threshold value.

11. The method of claim 10, wherein receiving, by the processor, the magnitude of the reflections comprises converting, using an analog-to-digital converter, the magnitude of the reflections into a digital signal.

12. The method of claim 10, wherein providing, by the processor, the indication of contamination comprises providing the indication on a communications bus.

13. The method of claim 7, wherein the optical system is an aircraft icing detection system.

14. The method of claim 7, further comprising blocking, using the photodetector, the reflections of the laser beam from reaching a receiver lens.

\* \* \* \* \*